United States Patent [19]

Fuhrmann

[11] Patent Number: 4,965,885
[45] Date of Patent: Oct. 23, 1990

[54] FILM CARRIER FOR ENDODONTIC DENTAL RADIOGRAPHS

[76] Inventor: Andreas Fuhrmann, Bellmannstrasse 32, 2000 Hamburg 52, Fed. Rep. of Germany

[21] Appl. No.: 87,163

[22] Filed: Aug. 19, 1987

[30] Foreign Application Priority Data

Jan. 28, 1987 [DE] Fed. Rep. of Germany ... 8701308[U]

[51] Int. Cl.[5] .............................................. G03B 42/04
[52] U.S. Cl. ...................................... 378/168; 378/208
[58] Field of Search ................................ 378/168–170, 378/208

[56] References Cited

U.S. PATENT DOCUMENTS

| | | | |
|---|---|---|---|
| 1,398,247 | 11/1921 | Wallace | 378/168 |
| 1,445,169 | 2/1923 | Ralph | 378/168 |
| 2,245,395 | 6/1941 | Goldberg | 378/170 |
| 2,753,461 | 7/1956 | Goldberg | 378/168 |
| 3,473,026 | 10/1969 | Updegrave | 378/170 |
| 4,251,732 | 2/1981 | Fried | 378/170 |
| 4,507,798 | 3/1985 | Welander | 378/168 |
| 4,554,676 | 11/1985 | Maldonado et al. | 378/147 |
| 4,592,084 | 5/1986 | McAuslan | 378/170 |
| 4,593,401 | 6/1986 | Colbery | 378/168 |
| 4,633,493 | 12/1986 | Linden | 378/168 |
| 4,707,847 | 11/1987 | Van Aken | 378/168 |

FOREIGN PATENT DOCUMENTS

8610962 4/1986 Fed. Rep. of Germany.

*Primary Examiner*—Janice A. Howell
*Assistant Examiner*—John C. Freeman
*Attorney, Agent, or Firm*—Toren, McGeady & Associates

[57] ABSTRACT

The film carrier for endodontic dental radiographs according to the parallel method comprises a U-shaped moulded body having a leg which is constructed as a bite-on block and having another, shorter leg which is constructed as a contact holding block, the web interconnecting the two legs being arcuately constructed in its lower portion and being formed as back plate for securing a dental X-ray film wherein the upper wall surfaces of the bite-on block and of the contact holding block form a plane with the dental X-ray film bearing surface, wherefore by raising and displaying the bite-on block in the mesial direction there will be space for root canal instruments, whereas the web-like contact holding block of the film carrier at the distal end by contact with the opposite jaw will ensure a better hold and an exact positioning of the film carrier in a patient's mouth whilst taking test radiographs.

2 Claims, 4 Drawing Sheets

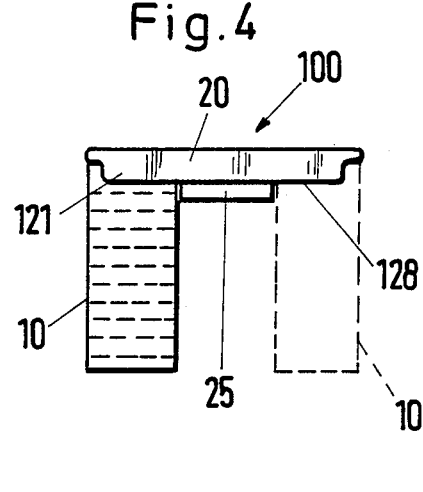
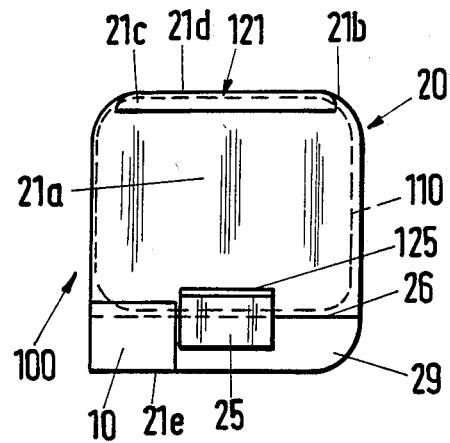
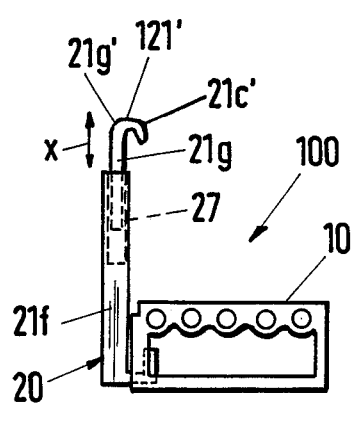
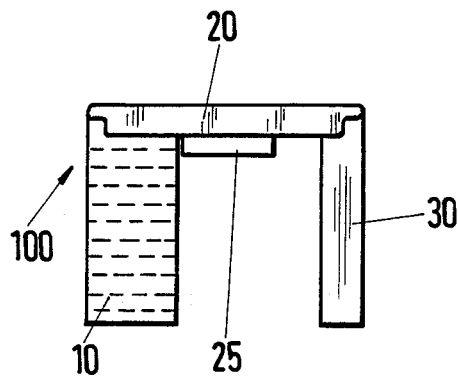

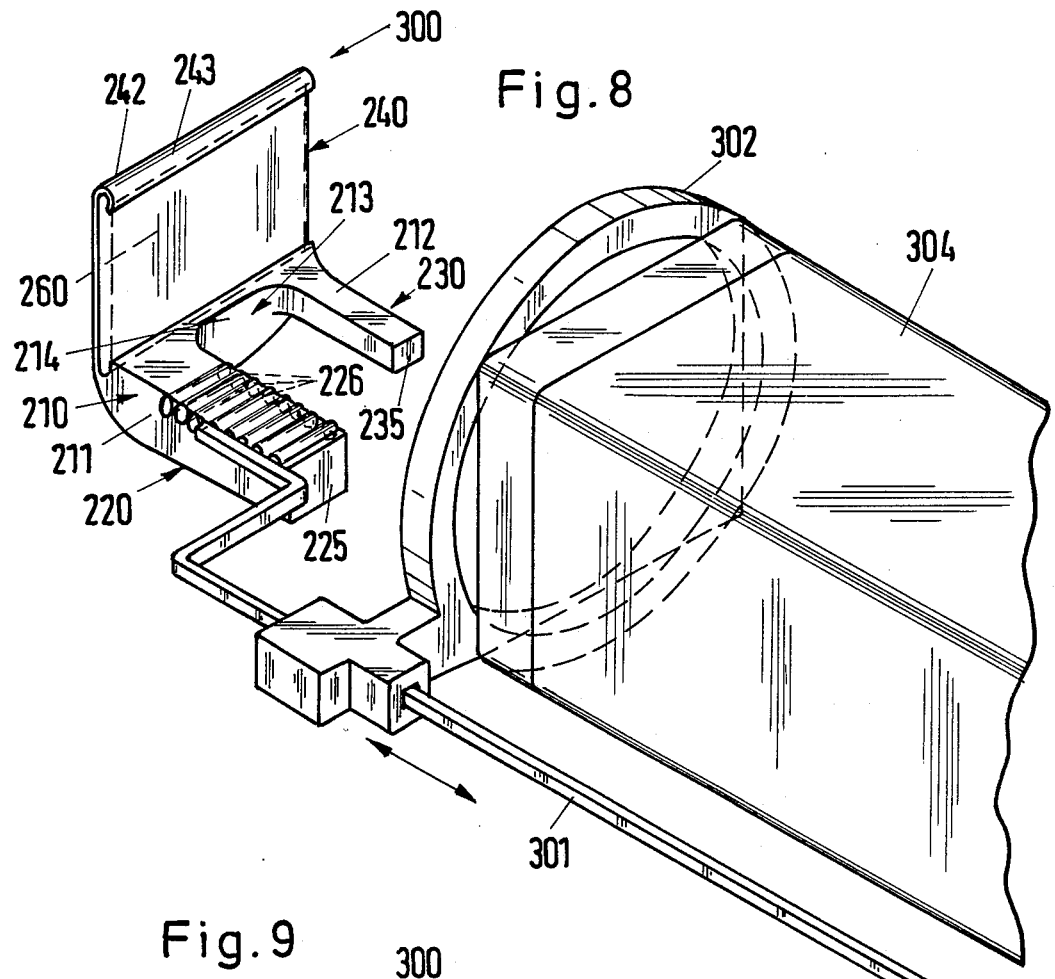

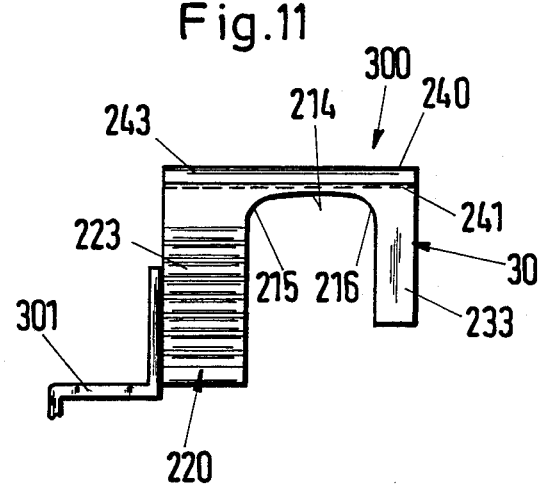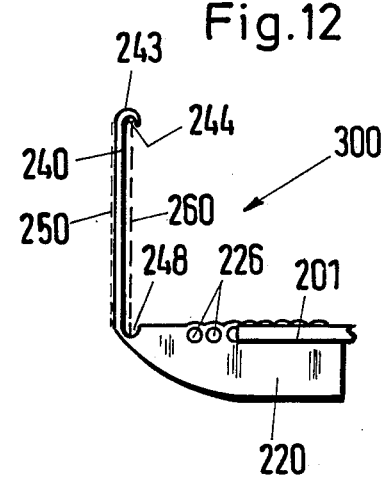

FILM CARRIER FOR ENDODONTIC DENTAL RADIOGRAPHS

BACKGROUND OF THE INVENTION

The present invention relates to a film carrier for endodontic dental radiographs in the parallel method, comprising a bite-on block, a back plate for mounting a dental X-ray film shaped onto said block and at right angles to the bite-on plane formed by said block, a guide rod held by means of a detachable plug-in fastening to the bite-on block and a sighting ring displaceable on the guide rod in its longitudinal direction and having a mounting support for fixing the film carrier to a cone of a dental X-ray examination unit.

In endodontia, for the purpose of showing a tooth, dental radiographs are made using X-ray examination units which are constructed for dental purposes. The linear measurement of the root canal being of great importance in endodontia. This linear measurement is determined with the aid of dental radiographs. The parallel method is the ideal way of taking test radiographs. In this X-ray recording method the central beam is directed at right angles onto the tooth axis and the film plane. Dental X-ray films have been developed for intraoral shots, which have a plate-like construction and standardized dimensions, so that the film can be introduced into the oral cavity. As a function of the position of the particular tooth which is to be photographed, the dental X-ray film plate is held by the patient in the each case necessary position following insertion into the mouth. This is brought-about by pressing the film by means of the thumb or index finger against the object to be photographed.

A film carrier with the aforementioned features has been developed more particularly for the use of the parallel method enabling the film to be introduced in such a way into the patient's mouth, that it is parallel to the longitudinal axis of the tooth. Due to the space conditions in the mouth, at certain points the film must be at a greater distance from the tooth and in order that this does not lead to distortions, it is necessary to increase the focus-film difference, which is effected by means of the extended cone on the X-ray tube, i.e. on the X-ray examination unit.

In the case of such film carriers, the film is held on a back plate, onto which is shaped a biting plate, by means of which the patient holds the film carrier by tooth pressure.

However, such film carriers are not suitable for test photographs with root canal instruments and/or cofferdam. Therefore, in general, endodontic photographs are produced by using the half-angle method, which is an X-ray recording method in which the central beam on the apex is directed at right angles to the angle bisector between the film plane and the tooth axis. However, this half-angle method often leads to unsatisfactory results, which applies both for the linear measurement of the root canal and for the reproducibility, because it is difficult to compare the different control photographs of a root treatment. In addition, the biting plates arranged centrally with respect to the film carrier back plate are so dimensioned and so arranged on the back plate, that it is not possible to use root canal instruments, because the needles used for preparing the root canal remain in the latter during radiography. The gripping end of said needles project from the root canal and come to rest in such a way in the vicinity of the biting plate of a film carrier inserted in a patient's mouth, that conventional film carriers cannot be used. In addition, the film carrier back plates have smaller dimensions than the dental X-ray films used, so that said film projects by a portion over the all-round edge to the back plate and as a result during radiography the film is bent by pressure action. A folding over or bending of the dental film leads to small electric discharges in the emulsion layer of the film, which can be revealed in the form of black lines on the developed film and can give rise to misinterpretations. Moreover, when biting together the teeth, the patient is subject to a pressure pain caused by the upper edge of the film introduced by means of the film carrier into the patient's mouth and whose relatively sharp edges come into contact with the sensitive mucous membranes of the gum and as a result of the marked pressure action causes pain. The patient often tends to escape the pain by reducing the biting pressure, which can in turn lead to a positional displacement of the film, although it is held in the film carrier.

Furthermore, film carriers for endodontic dental radiographs are known in numerous different forms. Thus, the film carrier according to US Pat. 4,593,401 comprises an approximately U-shaped moulded body which, in its web connecting the two legs is provided with a slot-like reception opening, which serves to receive the dental X-ray film. The film is secured in such a way that a small portion thereof is inserted into said slot-like recess in the carrier and is held therein. However, this film carrier does not solve the problem of bending, folding over and the like of the film, because there is no full-area engagement of said film on the mounting support. Moreover, this film carrier does not permit test radiographs in the upper jaw and radiographs using the parallel method.

U.S. Pat. No. 4.592.084 discloses a further film carrier with a biting plate, in which no back plate is provided for receiving the dental X-ray film. The film carrier is constructed as a U-shaped clamping holder securing a portion of the film. That region of the dental X-ray film which is not held by the film carrier clamp is unprotected, so that a bending and positional change to the film is possible, which can lead to inaccurate radiographs.

SUMMARY OF THE INVENTION

The object of the present invention is to provide a film carrier of the aforementioned type with increased patient comfort for endodontic test radiographs in the parallel method, and which has adequate space for receiving the root canal instruments. It is a further object to provide a carrier which permits an additional stabilization at the distal end and in which a planar mounting of the dental X-ray film is ensured, without the sharp edges of said film coming into contact with the sensitive mucous membranes of the hard gum. In addition, the film carrier must also permit test radiographs in the side tooth region and the full dental film surface should be available for such radiographs.

According to the invention this problem is solved in the case of a film carrier of the afore mentioned type in that the film carrier comprises a roughly U-shaped moulded body made of plastic having one leg construced as a bite-on block, another leg constructed as a contact holding block and a web interconnecting the two legs constructed as a back plate. The contact holding block is shorter than the bite-on block, and the bite-on block and the contact holding block have roughly square cross-sections, the cross-section of the bite-on block being larger than that of the contact holding block. The transition regions of the facing wall surfaces of the bite-on block and the contact holding block to the wall surface of the web connecting the bite-on block with the contact holding block are arcuately constructed. The back plate passes into a lower dental X-ray film bearing surface facing the bite-on block and the contact holding block and which has larger dimensions than said film, the upper edge of the back plate being slightly bent in the direction of the bite-on block and the contact holding block, accompanied by the formation of a dental X-ray film retaining groove, wherein the upper wall surfaces of the bite-on block and the contact holding block form one plane with the dental X-ray film bearing surfaces at the bottom, the bite-on block conically tapers from its front free end in the direction of the back plate and passes into the lower edge of said back plate, which passes into the bottom wall surface of the contact holding block.

Such a film carrier is characterised by four essential and advantageous features. There is space for the root canal instruments by raising and displacing the bite-on block in the mesial direction. There is additional stabilization at the distal end, the web-like contact holding block of the film carrier at the distal end by contact with the opposite jaw ensures a better hold and more exact positioning of the film carrier in a patient's mouth whilst taking test radiographs. The back plate is enlarged over and beyond the dental X-ray film size, so that the film does not bend and does not change its position through pressure. In addition, the sharp edges of the film pack can no longer come into contact with the sensitive mucous membranes of the hard gum. Since, contrary to the dental film, the back plate is widened and rounded at the upper edge, the patient no longer feels any pain on biting together. A better anatomical adaption when biting together is ensured by displacing the lower face of the contact holding block into a plane located above the plane formed by the lower face of the bite-on block, in the case of a conically tapering transition from bite-on block to contact holding block in the vicinity of the lower edge of the back plate.

The overall construction of the film carrier helps to improve patient comfort. This improved patient comfort mainly leads to a more stable position of the film carrier in the patient's mouth, because apart from the bite-on block and the web-like contact holding block at the distal end in the back plate the film holder holds a further support block, so that test radiographs are also possible in the side tooth region. The present film carrier in both the dentist's surgery and in the clinic contributes to making it easier to detect the correct preparation of the root canals, so that as a result the endodontic treatment is significantly improved.

BRIEF DESCRIPTION OF THE DRAWINGS

The invention is decribed in greater detail hereinafter relative to non-limitative embodiments and the attached drawings, wherein show:

FIG. 4 A view from above of the film carrier.
FIG. 5 A view from the front of the film carrier.
FIG. 6 A further embodiment of a film carrier with a size-variable back plate in a side view.
FIG. 7 A film carrier with a stabilizing web located at the distal end of the back plate in a view from above.
FIG. 8 A set of instruments comprising a rectangular cone and a film carrier in a perspective view.
FIG. 9 The film carrier in front view.
FIG. 10 The film carrier in rear view.
FIG. 11 The film carrier in a view from above.
FIG. 12 The film carrier in a side view.

DETAILED DESCRIPTION OF THE PREFERRED EMBODIMENTS

Figure 1:
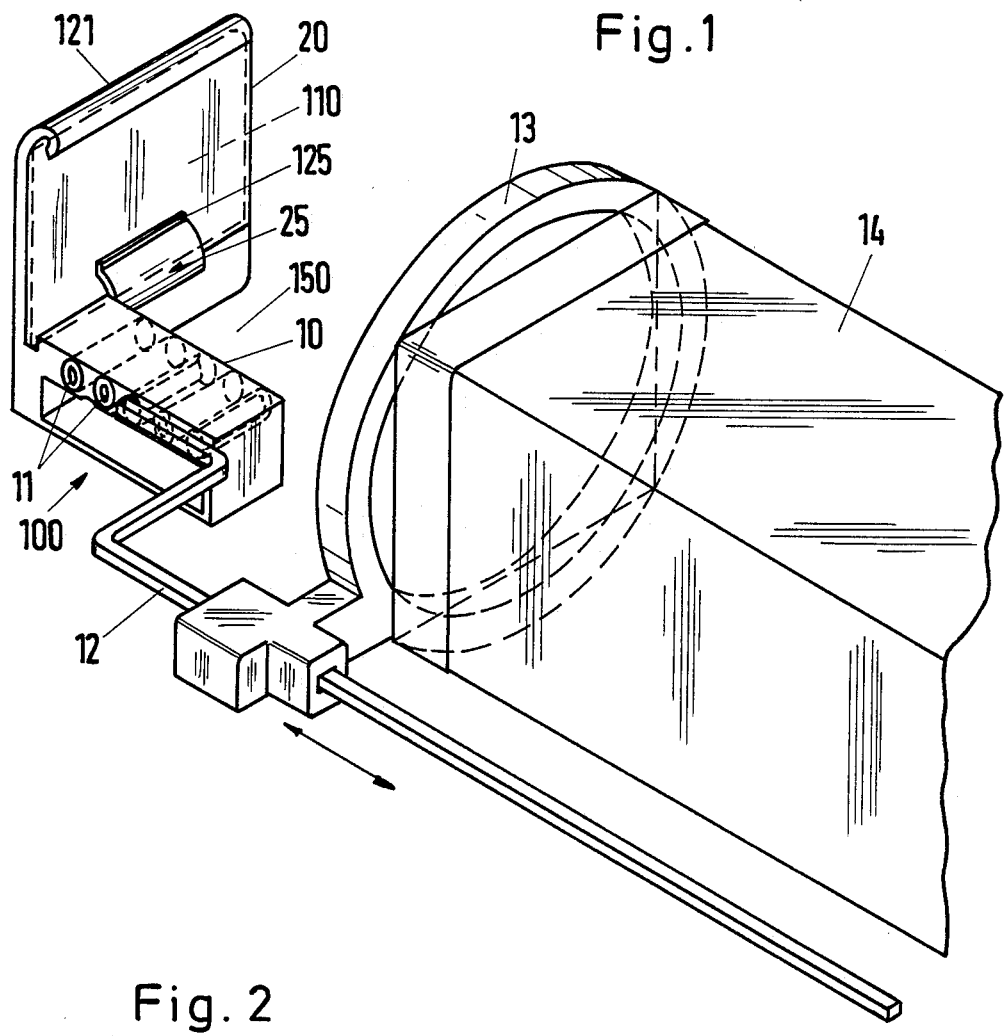
FIG. 1 An instrument set comprising a rectangular cube and a film carrier in a diagrammatic view.

FIG. 1 shows an instrument set for taking test radiographs in endodontics using the parallel technique, said instrument set comprising a film carrier 100, a guide rod detachably connected thereto, a sighting ring 13 held in the guide rod 12 and displaceable in the longitudinal direction thereof and a cube 14, to which the film carrier can be fixed by means of guide rod 12 and sighting ring 13. This cube 14 is part of a dental X-ray apparatus not shown in the drawing and said cube 14 can also be connected to such an apparatus.

Film carrier 100 comprises a back plate 20 for engaging and receiving a dental X-ray film 110 constructed in per se known manner and a biting plate 10 shaped on to the back plate 20, which is at right angles to the latter. This biting plate 10 also has a plurality of bores 11, which are parallel to one another and to the back plate 20 and which are used for receiving and securing the guide rod 12, as shown in FIG. 1. On the end of guide rod 12 facing biting plate 10 are formed two spaced pins, which can be inserted in bores 11 of biting plate 10, in order to hold the guide rod 12 on said biting plate and so as to be able to effect a length change.

Film carrier 100, i.e. its biting plate 10 and back plate 20 are made from plastics, particularly tetrafluoroethylene or other suitable plastics or materials.

Figure 2:
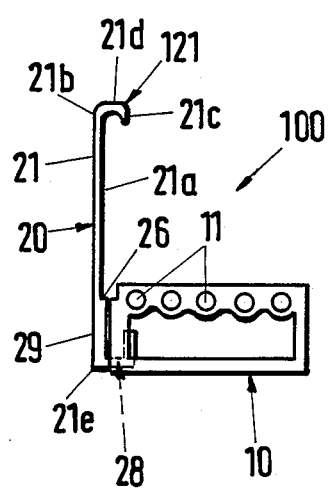
FIG. 2 A side view of the film carrier.
Figure 3:
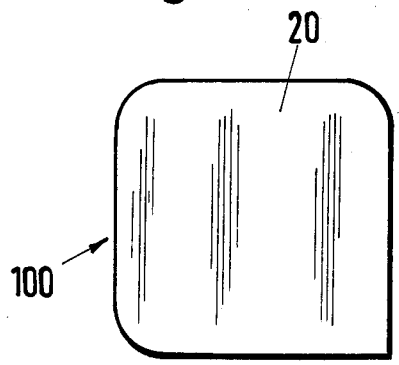
FIG. 3 A rear view of the film carrier.

According to FIGS. 2 to 5, the back plate 20 of film carrier 100 comprises a plate-like blank 21 with a blank surface 21a corresponding to the size of the dental X-ray film 110 used. The upper edge 21b of the plate-like blank 21 of back plate 20 is bent in U-shaped manner towards biting plate 10, accompanied by the formation of an arcuate, i.e. rounded profile, in such a way that said rounded edge region overlaps at the top the inserted film 110 and also holds it on back plate 20. The leg 21c of the U-shaped edge profile parallel to the plate-like blank 21 is constructed as a resilient-elastic clamping strip 121, the clamping action of said strip 121 resulting from the resilient-elastic nature of the material from which film carrier 100 is made. The upper web 21d of the U-shaped edge profile interconnecting the two legs 21c and 21a is rounded (FIG. 2).

In its lower region, the plate-like blank 21 of back plate 20 has a lengthened portion 29 extending over the entire length of back plate 20 and on which is arranged the subsequently described biting plate 10. The height of the extended portion 29 roughly corresponds to the height of biting plate 10. In the transition region of blank surface 21a to the extended portion 29 is provided a further clamping holder 25, which has a resilient-elastic clamping strip 125. The clamping holder 25 being constructed in such a way that the film 110 to be held on to back plate 20 can be inserted into the upper opening of holder 25 and is held in position by the tongue-like leg of clamping strip 125 which is under clamping action. Due to the fact that the dental X-ray film 110 is held on the one hand by the U-shaped edge profile 121 and on the other by the clamping holder 25 on the back plate 20, there is no possibility of the film 110 moving during radiography when the film carrier 100 is placed in the patient's mouth. The clamping holder 25 is made from the material of back plate 20 or film carrier 100, so that the clamping action of clamping strip 125 of clamping holder 25 is obtained as a result of the resilient-elastic material used. The upper edge of the back plate 20 provided with the extended portion 29 is indicated at 21e in FIG. 5. The plate-like blank 21 of back plate 20 is also provided with rounded corner regions. Biting plate 10 of film carrier 100 has a block-like construction, as can be gathered from FIGS. 1, 4 and 5. This block-like biting plate 10 serves the function of a bite on block and is shaped on to the back plate 20 of film carrier 100 or is detachably connected to the back plate 20 according to another embodiment. The arrangement of biting plate 10 on back plate 20 is such that the biting plate is arranged laterally displaced with respect to the center of said back plate 20. Due to this displaced arrangement of the biting plate 10, a large lateral opening 150 is obtained (FIG. 1), so that when the film carrier 100 is in use, root channel instruments inserted in the root channel can project into said lateral recess or opening 150, without it being necessary to change the position of film carrier 100 in the patient's mouth. The block-like biting plate 10, which virtually forms a web, has a height roughly corresponding to one-third or one half of the height of back plate 120. As the biting plate 10 is positioned in the vicinity of the lower extended portion 29 of back plate 20, the further blank surface 21a of the plate-like blank 21 of back plate 20 is available for receiving the dental X-ray film 110. In the transition region of said blank surface 21a of plate-like blank 21 to the extended portion 29 is formed a horizontally directed bearing edge 26, on which can be engaged the film 110 to be used (FIG. 5). This bearing and boundary edge 26 is shaped from the material of back plate 20 ad constitutes a step-like member. The height of the biting plate 10 roughly corresponds to the height of the extended portion 29 of the plate-like blank 21 of back plate 20, so that the full blank surface 21a is available for film 110. The width of biting plate 10 roughly corresponds to ⅓ of the length of back plate 20.

The block-like biting plate 10, which is provided on its top surface with a gripping profile not shown in the drawings, is connected in a fixed or detachable manner to the back plate 20 of film carrier 100 so that on biting on, it is ensured that the carrier 100 cannot slip within the patient's mouth. For detachable connection purposes, a plug connection indicated at 28 in FIG. 2 is provided and by means of this the biting plate 10 can be fixed to back plate 20, but other fixing means can also be used, e.g. detachable screw connections. When using a plug connection use can be made of the resilient elastic action of the material of the film carrier 100 for the firm mounting of biting plate 10 on back plate 20, so that as result of tongue-like resilient-elastic legs, the biting plate 10 is held by means of clamping action, accompanied by the formation of corresponding guides on the plate-like blank 21 of back plate 20.

The detachable fitting of biting plate 10 on back plate 20 permits the changing of biting plate 10, if corresponding means for producing the plug connection are provided at the free end of back plate 20. This is indicated at 128 in FIG. 4. The biting plate 10 transferred to back plate 20 is shown in broken line form. This construction permits a universal use of film carrier 100.

In order to be able to adapt back plate 20 to the different sizes of the dental X-ray films used, according to the embodiment shown in FIG. 6, the back-plate 20 of film carrier 100 comprises two plate-like blanks 21f, 21g. The block-like biting plate 10 is arranged on the lower, larger plate-like blank 21f. The upper, narrower plate blank 21g is displaceably held in the direction of arrow X in the lower plate blank 21f. For this purpose, blank 21f is provided with guides indicated at 27, which permit a holding and displacement of blank 21g. Plate blank 21g is insertable or extractable to adapt to the particular height of the film used. In the particular inserted or extracted position, it is possible to fix blank 21g. For fixing purposes, it is e.g. possible to use a rack-like stop or locking profile, which engages in a corresponding counterprofile. However, it is also possible to utilize the clamping action of plate blank 21g in plate blank 21f as a result of the material used for producing the film carrier100 and the resulting increased friction.

The upper edge 21g' of blank 21 g is bent in the direction of biting plate 10, so as to form a U-shaped edge profile, so that the bent leg 21c' facing plate 10 has the effect of a resilient-elastic clamping strip. This clamping strip 121', in the same way as clamping strip 121 of the film carrier embodiment shown in FIG. 2, leads to a reliable top securing of the inserted dental X-ray film 110. In the same way in which the back plate 20 can undergo height modification, it is possible to vary the length of back plate 20, so that it is possible to use films of any size in film carrier 100. The two clamping strips 121, 121' need not have a clamping action and can also be constructed in such a way that the film 110 is not held in clamping manner.

In the case of the embodiment shown in FIG. 7, a web 30 is arranged at the distal end of back plate 20, which is constructed in much the same way as the block-like biting plate and is made from the same material as film carrier 100. This web 30 can be connected in fixed or detachable manner to back plate 20. The gap between biting plate 10 and web 30 receives the root channel instruments projecting from the root channel.

The dimensions of back plate 20 can also be such that after inserting and fitting dental X-ray film 110, back plate 20 projects over the dimensions of said film.

A film carrier constructed in the aforementioned manner makes it possible to make test radiographs according to the parallel technique. Due to the fact that the biting plate is laterally displaced with respect to the back plate, there is sufficient space for the root channel instruments, which can remain in the root channel during radiography. Particularly through the heightening and displacing the block-like biting plate towards the mesial, sufficient space is provided for the root channel instruments. The securing of the film carrier in the patient's mouth is considerably improved by the block-like constructing of the biting plate and this contributes to stabilizing the film position in the mouth. By increasing the size of the back plate over and beyond that of the film size, it is ensured that the film does not bend and does not change position due to pressure. Moreover, the sharp edges of the dental X-ray film or film pack can no longer come into contact with the sensitive mucous membrane of the hard gum, this greatly being helped by the upper edge of the back plate being widened and rounded with respect to the film. When the film carrier is inserted in the patient's mouth, the patient no longer feels any pain when he has to bite the teeth together. This improved patient comfort ensures a more stable position of the film carrier, because the latter, as well as the biting plate or the bite-on block forming the latter, according to a further embodiment of the invention is provided on the distal end on the back plate with a web running parallel to the bite-on block and spaced therefrom, the film carrier thereby receiving a further support point. This web leads to an additional stabilization at the distal end, in that at the latter by the web contacting the opposite jaw, a better hold and more exact positioning are ensured.

Through the use of a film carrier constructed in this way, both in dental practice and in clinics and for student training, it is more easily possible to reveal the correct preparation of the tooth channels, which significantly increases the possibility of successful endodontic treatment. The film carrier is particularly intended for the back teeth, but due to the detachable fixing of the biting plate to the back plate and the interchangeability possibility, the film carrier can also be used in connection with the front teeth.

Further developments of the invention are characterized in the subclaims.

FIG. 8 shows a set of instruments for performing test radiographs in endodontia using the parallel method, said instrument set comprising a film carrier 300, a guide rod 301 detachably connected thereto, a sighting ring 302 held on guide rod 301 and displaceable in the longitudinal direction of the latter and a cone 304, to which film carrier 300 can be fixed by means of guide rod 301 and sighting ring 302. This cone 304 forms part of a dental X-ray examination equipment, not shown in the drawing and said cone 304 can also be connected to said unit.

Film carrier 300 comprises a roughly U-shaped moulded body 210 made from plastic and in particular tetrafluoroethylene or some other suitable plastic or material. The U-shaped moulded body 210 has two legs 211, 212 and a web 213 connecting said two legs. Leg 211 is constructed as a bite-on block 220, leg 212 as a contact holding block 230 and web 213 as a back plate 240, so that the film carrier 300 is formed by bite-on block 220, contact holding block 230 and back plate 240 for securing a dental X-ray film 260.

The contact holding block 230 is shorter than the bite-on block 220. Both blocks 220, 230 are shaped parallel to one another on the back plate 240. Both the bite-on block 220 and the contact holding block 230 have roughly square cross-sections, but the cross-section of bite-on block 220 is larger than that of contact holding block 230 (FIG. 9).

Bite-on block 220 comprises a parallelepipedic or rectangular moulded body with a roughly square cross-section. The outer wall surface of bite-on block 220 is designated 221, its inner wall surface 222, its upper wall surface 223, its lower wall surface 224 and its free end 225. Bite-on block 220, which is at right angles to the back plate 240, has a plurality of through-bores 226, which are parallel to one another and to back plate 240, which serve to receive and secure guide rod 301, which has the bent construction shown in FIG. 8. On the end of guide rod 301 facing bite-on block 220 there are preferably two spaced pins or studs, which are not shown in the drawing and which can be inserted in the through-bores 226 in bite-on block 220, in order to maintain guide rod 301 on bite-on block 220 and in order to be able to effect a spacing change between film carrier 300 and cone 304.

Contact holding block 230 preferably comprises a rod or web-like moulded body with a square cross-section and runs parallel to the bite-on block 220. Contact holding block 230 passes into back plate 240 in the lower region of the latter. The outer wall surface of contact holding block 230 is designated 231, its inner wall surface 232, its upper wall surface 233, its lower wall surface 234 and its free end 235. The transition regions 215, 216 of the vertical inner wall surfaces 222, 232 of bite-on block 220 and contact holding block 230 to the inner wall surface 214 of web 213 or the back plate 240 are arcuately shaped. However, the spacing between the bite-on block 220 and the contact holding block 230 is such that there is adequate space for receiving, the root canal instruments. However, on the other side, their overall dimensions of the film carrier are such that the outer boundaries of the film carrier are given by the back plate 240 for receiving the dental X-ray film 260.

Back plate 240 has a square or rectangular surface, its film reception surface being designated 249 and its upper edge 242. Upper edge 242 of back plate 240 is bent in the direction of bite-on block 220 and contact holding block 230, whilst forming a dental X-ray film holding groove 244 which is accessible from below, the bent portion being indicated at 243 in FIG. 8. The upper edge design in conjunction with the dental film holding groove 244 is such that a dental film 260 placed on the reception surface 249 of back plate 240 engages with its upper edge portion into the dental film holding groove 244 and is secured in position by means of said bent portion 243. The dimensions of the back plate 240 are somewhat larger than those of conventional dental X-ray films, so that a film 260 held on back plate 240 by its all-round or lateral edges does not project over the lateral edges 246, 247 of back plate 240.

In the lower transition region of back plate 240 to the upper wall surfaces 223, 233 of bite-on block 220 and contact holding block 230 is formed a dental film bearing surface 241, which is contructed as a through step, i.e. which projects towards the bite-on block 220 and the contact holding block 230 and which has a width roughly corresponding to that of a commercially available dental film, so that after engaging a dental film 260 on back plate 240, said film is firstly held in the retaining groove 244 of back plate 240 and secondly and simultaneously on the lower bearing surface 241. This dental film bearing surface 241, which virtually forms the inner lower edge 245 of back plate 240, can also be contructed as a channel, slot, etc. 248 (FIG. 12), in order to ensure that the dental X-ray film 260 is secured in film carrier 300.

The dental X-ray film 260 is then inserted in the film retaining groove 244 and in the channel-like film bearing surface by slightly bending down the said film. After inserting the film in the retaining groove 244 and the channel-like bearing surface, said dental film moves back out of the slightly bent state, so that it engages flat on the dental film bearing surface 241 of back plate 240.

Biting block 220 and contact holding block 230 form with their upper wall surfaces 223, 233 a horizontal plane, in which is located the dental X-ray film bearing surface 241 of back plate 240 (FIG. 9). The bite-on block 220 in the vicinity of its bottom, i.e. lower wall surface 224 from its free end 225 to its rear region, i.e. to the lower edge 245 of back plate 240 in a conically tapering manner. In the rear region, the lower part of back plate 240, as shown in FIG. 10 also conically tapers towards the contact holding block 230. Through this raising and displacement of the bite-on block 220 in the mesial direction, not only is adequate space provided for receiving the root canal instruments, but an additional stabilization is obtained at the distal end. In this way when the film carrier is inserted, the contact holding block 230 at the distal end ensures improved contact with the opposite jaw, which in turn leads to a better hold and a more exact positioning of the film carrier in the patient s mouth. Thus, the film carrier acquires a more stable position when corresponding biting action takes place. Apart from the bite-on block and contact holding block at the distal end in the back plate the film carrier receives an additional support point, so that any displacement of the film carrier during radiography is prevented.

Advantageously back plate 240 of film carrier 300 is made from a radiopaque material. For this purpose, the plastic used for producing the back plate 240 can be provided with a substance through which it is difficult for X-rays to pass, namely in the form of admixtures of barium sulphate, gypsum, bismuth compounds, etc. The back plate 240 can also be provided with a radiopaque coating 250 (FIG. 12), which is preferably provided on the rear outer wall surface of back plate 240 (FIG. 12). This coating 250 can e.g. be in the form of a thin lead plate, but which can also be incorporated into the plastic material from which the back plate is made.

The back plate 240 is somewhat larger than the dental X-ray film. The height of the back plate 240 corresponds to the height of the film, whilst the back plate is wider than the film. Due to the fact that the dental X-ray film 260 is held in the upper region by the bent down edge portion 243 of the back plate and is supported in the lower region against the film bearing surface, the full dental film surface is available for test radiographs. The additional clamping holder does not lead to any loss of dental film surface.

In any of the previously discussed embodiments the bite-on block preferably has a height equal to roughly ⅓ or κ the height of the back plate, and a width equal to roughly ⅓ the back plate length. This relationship being most apparent in FIG. 10.

What is claimed is:

1. A film carrier for endodontic dental radiographs by a parallel comprising:
    a plastic U-shaped molded member having a first leg forming bite-one block, a second leg forming a contact holding block, and a web which connects said legs provided as a backplate which is at a right angle to a bite-on plane formed by the bite-on block, said backplate being provided so as to retain a dental x-ray film, said backplate includes a lower x-ray film bearing surface arranged so as to face the bite-on block and an upper edge bent slightly in a direction towards the bite-on block so as to form an x-ray film holding groove, said backplate being dimensioned larger than the x-ray film, said contact holding block having a length shorter than that of said bite-on block, said bite-on block and said contact holding block each having a square cross-section, the cross-section of said bite-on block being larger than the cross-section of said contact holding block, said bite-on block and said contact holding block having opposing wall faces which have curved transitional regions that extend towards a walls surface of said web connecting said bite-on block and said contact holding block, said bite-on block and said contact holding block each having an upper wall surface area in a common plane with the lower dental film bearing surface, said bite-on block having a free end and a bottom side which tapers from the free end toward said backplate in a conical manner so as to extend into a lower edge of said backplate which in turn extends into a bottom side wall surface of said contact holding block, said backplate being opaque to x-rays;
    a guide rod detachably held on said bite on block by a plug-in connection; and
    a sighting ring displaceable along said guide rod and having a mounting support so that the film carrier is fixable to a barrel of a dental x-ray apparatus.

2. A film carrier as defined in claim 1, wherein the film bearing surface is provided so as to form grooves.

* * * * *